(12) United States Patent
Van Stevendaal et al.

(10) Patent No.: US 10,458,926 B2
(45) Date of Patent: Oct. 29, 2019

(54) CALIBRATION HARDWARE PHANTOM FOR DIFFERENTIAL PHASE CONTRAST IMAGING

(71) Applicant: KONINKLIJKE PHILIPS N.V., Eindhoven (NL)

(72) Inventors: Udo Van Stevendaal, Ahrensburg (DE); Heiner Daerr, Hamburg (DE); Thomas Koehler, Norderstedt (DE); Gerhard Martens, Henstedt-Ulzburg (DE); Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 166 days.

(21) Appl. No.: 15/311,886

(22) PCT Filed: May 18, 2015

(86) PCT No.: PCT/EP2015/060822
§ 371 (c)(1),
(2) Date: Nov. 17, 2016

(87) PCT Pub. No.: WO2015/180977
PCT Pub. Date: Dec. 3, 2015

(65) Prior Publication Data
US 2017/0122885 A1      May 4, 2017

(30) Foreign Application Priority Data
May 27, 2014 (EP) .................... 14170046

(51) Int. Cl.
*G01N 23/00* (2006.01)
*G01N 23/04* (2018.01)
(Continued)

(52) U.S. Cl.
CPC ............. *G01N 23/04* (2013.01); *A61B 6/484* (2013.01); *A61B 6/583* (2013.01); *G01N 23/041* (2018.02); *G01N 2223/3035* (2013.01)

(58) Field of Classification Search
CPC ........................ G01N 2223/3035; A61B 6/583
See application file for complete search history.

(56) References Cited

U.S. PATENT DOCUMENTS 6,064,716 A * 5/2000 Siffert .................. A61B 6/482
378/207
2011/0243302 A1   10/2011 Murakoshi
(Continued)

FOREIGN PATENT DOCUMENTS

| JP | 2002223318 A | 8/2002 |
|---|---|---|
| JP | 2004245623 A | 9/2009 |
| WO | 2013027138 | 2/2013 |

OTHER PUBLICATIONS

F. Pfeiffer et al in "Phase retrieval and differential phase-contrast imaging with low-brilliance X-ray sources," Nature Phys. Lett. 2, 258-261 (2006).

(Continued)

*Primary Examiner* — Dani Fox
(74) *Attorney, Agent, or Firm* — Larry Liberchk (57) ABSTRACT

A phantom body (PB) for use in a differential phase contrast imaging apparatus (IM) for calibration of same. The phantom body (PB) allows for simultaneous calibration of three different image signal channels, namely refraction, phase shift and small angle scattering.

16 Claims, 6 Drawing Sheets

(51) Int. Cl.
*A61B 6/00* (2006.01)
*G01N 23/041* (2018.01)

(56) References Cited

U.S. PATENT DOCUMENTS

2011/0243305 A1  10/2011  Tada
2013/0236079 A1   9/2013  Carlsen

OTHER PUBLICATIONS

E Roessl et al, "Clinical boundary conditions for grating-based differential phase-contrast mammography", Philosophical Transactions of The Royal Society (A) Mathematical, Physical and Engineering Sciences, Mar. 6, 2014, vol. 372 No. 2010.
Schleede, "Multimodal hard X-ray imaging of a mammography phantom at a compact synchrotron light source", Journal of Synchrotron Radiation, vo. 13, No. 4, May 10, 2012.
"Gammex 156 Mammographie Accreditation Phantom", Gammex Products Catalog, 2014, pp. 115-116, XP055199173, Retrieved from the Internet: URL : http ://www.gammex.com/ace-files/ Gammex Catalog.pdf.
Bech M et al: "Advanced contrast modalities for X-ray radiology: Phase-contrast and dark-field imaging using a grating interferometer", Zeitschrift Puer Medizinische Physik, Urban Und Fischer, Jena, DE, vol. 20, No. 1, Jan. 15, 2010.
Pfeiffer et al: "Grating-based X-ray phase contrast for biomedical imaging applications", Zeitschrift Für Medizinische Physik, vol. 23, No. 3, Feb. 28, 2013.

\* cited by examiner

CALIBRATION HARDWARE PHANTOM FOR DIFFERENTIAL PHASE CONTRAST IMAGING

CROSS REFERENCE TO RELATED APPLICATIONS

This application is the U.S. National Phase application under 35 U.S.C. § 371 of International Application No. PCT/EP2015/060822, filed May 18, 2015, published as WO 2015/180977 on Dec. 3, 2015, which claims the benefit of European Patent Application Number 14170046.8 filed May 27, 2014. These applications are hereby incorporated by reference herein.

FIELD OF THE INVENTION

The invention relates to a phantom body configured for calibration of a phase contrast imaging system, to a phantom body system and to a use of a phantom body for calibration of a phase contrast imaging system.

BACKGROUND OF THE INVENTION

Electro-magnetic radiation such as x-ray radiation, when passing through matter, experiences three types of disturbances: there is absorption, there is refraction (that is, the phase of the radiation wave front experiences a shift) and there is a type of scattering, also called "small angle scattering".

Traditional radiography focused solely on the absorption disturbances. Recently, differential phase contrast techniques and related imagers have been devised that allow imaging all three of those disturbances and capture respective contrasts in separate images. The phase contrast image affords soft tissue discrimination superior to traditional, solely absorption based imagery. It has been observed also that despite the excellent imaging prospects the uptake, especially in the medical fields, have been not as enthusiastic as one may have expected. One reason for this may be that calibration procedures prove rather cumbersome for differential phase contrast imaging system because of required interferometric equipment (essentially a plurality of gratings). Some calibration procedures are based on so called "phantoms" such as described in US 2011/0243305.

SUMMARY OF THE INVENTION

There may therefore be a need for phantoms to conduct calibration procedures in differential phase contrast imaging systems more efficiently.

The object of the present invention is solved by the subject matter of the independent claims where further embodiments are incorporated in the dependent claims. According to one aspect of the invention there is provided a phantom body configured for calibration of a phase contrast imaging system, the system capable of emitting an X-ray beam, the phantom body comprising at least three mutually distinct parts configured for together causing a plurality of disturbances with respect to the X-ray beam when said X-ray beam passes through the phantom body, said plurality of disturbances including i) a phase shift, ii) an absorption and iii) a de-coherence, wherein any-one of the disturbances i), ii) and iii) is being caused by exactly one part of the at least three mutually distinct parts to a degree larger than other degrees with which said any-one of the disturbances is being caused by the respective two other parts of the at least three mutually distinct parts. The three disturbances i), ii) and iii) manifest themselves as three different physical effects each measurable by three respective imaging quantities/parameters recoverable by analyzing for instance a varying intensity signal at pixels of a detector, the variation being caused by using interferometric phase contrast imaging equipment. What is proposed herein is a phantom body where the different parts thereof are dedicated to different ones of the (at least) three physical effects. In other words, each of those parts responds to exactly one of the three effects at a higher degree or amount than the other two parts would do for the same effect. In other words, the phantom body allows calibrating the phase contrast imaging system simultaneously for each of the three imaging parameters that are derivable by signal processing of the detector signals. The degree or amount of disturbance is measurable for instance by the magnitude of the numerical quantities that can be computed from sampling an interference pattern by interferometric equipment. Furthermore, at least one part of the at least three mutually distinct parts comprises at least three distinct sub-parts configured to graduate the respective degree of disturbance caused by said part into three different sub-degrees. In other words, the three different degrees of the disturbance caused by the three different sub-parts of any given part may be different from each other, however, each of them is still higher than the same type of disturbance caused by any part or sub-part of the remaining two parts. For instance, the three sub-parts of the absorption part may cause respectively a high, a medium and a low level of absorption. However, each of the high, low and medium absorption is still higher than any of the absorption caused by the remaining two parts or their sub-parts. Having for each disturbance separate and distinct levels or degrees (of said disturbance) allows a more stable curved fitting when processing the detector signals received at the detector pixels after passage of the radiation through the phantom body. Each of the three different degrees of disturbance of the same type furnishes, per pixel, a local "pool" of three or more fitting variables that can be fitted more robustly to the signals observed at the various detector pixels. The sub-parts and parts as used herein are distinct in the sense that the respective disturbance levels caused by each of those parts do not transition smoothly from one part to the other but there is a discontinuity when one transition from one part to the other. This affords more accurate calibration because the three disturbances can be accurately calibrated for without (or at least with minimal) mutual cross-influence.

According to one embodiment, at least one part of the at least three mutually distinct parts is formed from one or more cuboids. According to one embodiment, at least one part of the at least three mutually distinct parts is formed from one or more rotation symmetric solids.

A rotation symmetric arrangement of the solids defining the various parts and sub-parts of the phantom body may be useful in computed tomography (CT) imaging systems so that calibration can be conducted along each projection direction as the x-ray source orbits around the examination region.

According to one embodiment, the phantom body is symmetric. Arranging the phantom body in a symmetric (for instance mirror symmetric manner) allows individually calibrating the respective sides, to the left or right of the axis, of different grid portions of a grid in a differential phase contrast interferometer.

According to one embodiment, the three or more sub-parts of at least one part of the at least three mutually distinct parts are grouped together.

According to one embodiment, the three or more sub-parts of at least one part of the at least three mutually distinct parts are interleaved with one or more sub-parts from at least another one of the two other parts of the at least three mutually distinct parts.

The various sub-parts of the three types of parts maybe either grouped separately into three separate groups or may be interleaved. This allows better adaptation of the phantom body to the space requirements of the imaging system to be calibrated. The sub-parts are either permanently fixed on a ground plate, or are non-destructably removable there from to allow re-grouping at leisure. For instance, the phantom body may have the look and feel of a calibration kit in which the parts or sub-parts can be clicked or otherwise snap-fitted onto the ground plate to define a physical structure of the phantom that fits the current requirements.

According to one embodiment, the part of the at least three mutually distinct parts that causes the highest degree of phase contrast disturbance, is formed from a plurality of wedges each wedge having a different wedge slope gradient configured to cause a different phase gradient and each wedge forming one of the sub-parts of said part.

The plurality of wedges can be either formed monolithically by cutting or milling same from a single block. Alternatively, the wedges may be formed as separate parts and are than either glued together, either side-by-side (in a plane perpendicular to the propagation direction of the incoming X-ray radiation) or may be stacked on top of each other along an axis defined by said propagation direction) according to requirement. The wedges may be positioned so as to contact each other or may be placed discretely so as to leave gaps between certain or any two neighboring wedges.

According to one embodiment, at least one of the wedges is formed as a double wedge with opposed slope gradients. In one embodiment there is a plurality of such double wedges that are either laid out adjacent each other (either contiguous or with gaps in between any two double wedges) or are placed on top of each other.

Stacking the wedges (whether or not they are double wedges) on top of each other allows forming a "phase shift booster" to increase the phase shift as required because the passing wave front will experience phase shift contributions from each of the stacked up (double-)wedges.

According to one embodiment, at least one of the parts is formed from any one of i) Polycarbonate, ii) Poly-methyl-methacrylate (PMMA), iii) Aluminum and iv) epoxy resin.

According to one embodiment, the part of the at least three mutually distinct parts that causes the highest degree of de-coherence disturbance, is formed from a structure having a plurality of air enclosures.

Preferably a polycarbonate (such as PMMA) or aluminum is used for the absorption and/or face shift part. Preferably an epoxy-resin with air enclosures such as bubbles or other porous structures are used for the part that is earmarked to cause the high degree of scattering. If the average diameter of the air enclosures is chosen large enough said porous material may also be used for the phase shift part.

In one embodiment a plurality of different phantom body "primitives" are mounted together on a common ground plate to so form a "complex" phantom that can be used to calibrate across a relatively large grating system such as grating tiling used for imaging system where a relatively large field of view is required.

According to one embodiment, there is a gap or security margin between each of the parts and/or sub parts thereof so as to increase the accuracy of the calibration procedure. This allows, for instance, ensuring that the underlying detector pixels receive signals that have passed through only one of the parts.

According to one embodiment, the phantom body's parts are defined or mounted on a common ground plate.

According to one aspect, a phantom body system is provided including a plurality of phantom bodies as previously described, said phantom bodies being mounted on a common ground plate. According to one embodiment, the plurality of phantom bodies are arranged on said plate in a symmetric manner.

In summary what is proposed herein is a phantom body, more particularly a single phantom body that comprises at least three different parts each dedicated to a single one of the three disturbances or physical effects of radiation-matter interaction, in other words rather than having three different separate phantoms each dedicated to only one of those parts the combined approach is taken herein so as to be able to simultaneously calibrate a given differential face contrast imager for each of the three image channels. The different parts and their sub-parts are combined into a single phantom body (e.g. by being mounted on said common ground plate) to assist ease of use and for enhanced practicality. The phantom body, the phantom body system and the use of the phantom body or the phantom body system, particular allow for successful application in medical imaging including but not limited mammography and CT.

BRIEF DESCRIPTION OF THE DRAWINGS

Exemplary embodiments of the invention will now be described with reference to the following drawings, which are not necessarily to scale, wherein.

DETAILED DESCRIPTION OF EMBODIMENTS

Figure 1:
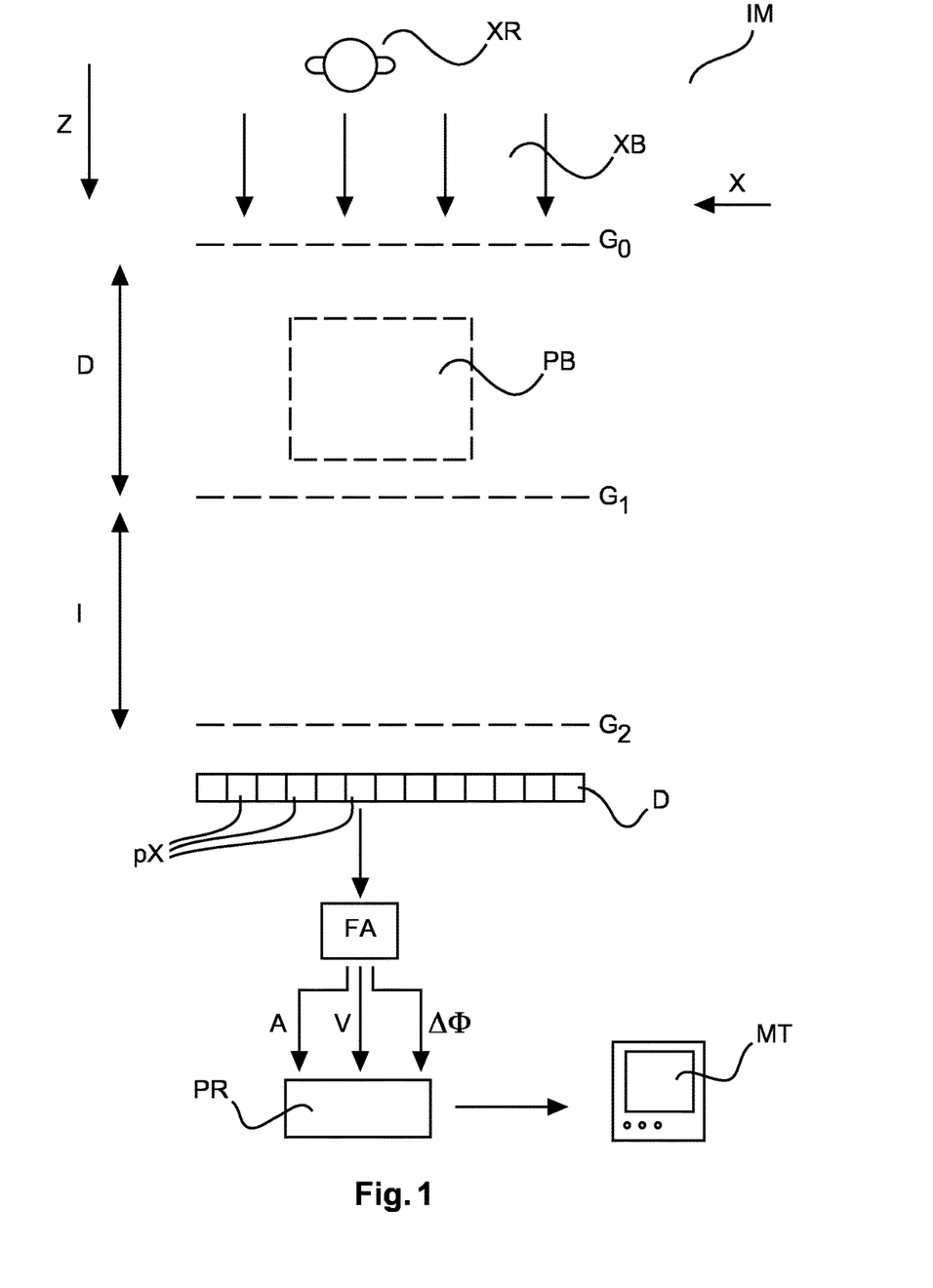
FIG. 1 shows components of a phase contrast imaging system.

FIG. 1 shows basic components of an imaging system IM with phase contrast imaging capabilities, in particular differential phase contrast imaging (DPCI). There is an X-ray source XR for generating X-ray radiation waves XB that, after passage through an examination region, are detectable by detector pixels px of a detector D. The phase contrast imaging capability is achieved by arranging an interferometer between the X-ray source XR and the radiation sensitive detector D.

The interferometer (which in one unlimiting embodiment is of the Lau-Talbot type) includes two or more, preferably, three gratings $G_0$, $G_1$ and $G_2$. The first attenuation grating $G_0$ at the X-ray source side has a period p0 to match and cause spatial coherence of the X-ray radiation wave front emitted at the X-ray source XR.

An absorption grating $G_1$ (having period p1) is placed at distance D from the X-ray source and causes an interference pattern with period p2 further downstream. Said interference pattern can be detected by detector D. Now, when a sample (to be imaged) is introduced in the examination region between the X-ray source and the detector, the phase of the interference pattern is then shifted. This interference pattern shift dip (as has been reported elsewhere, for instance in F M Epple et al, Unwrapping differential X-ray phase contrast images through phase estimation from multiple energy data, OPTICS EXPRESS, 2 Dec. 2013, Vol 21, No 24) is proportional to the gradient of the phase shift OA due to the accumulated refraction along respective paths through the sample (hence the name DCPI). In other words, if one were then to measure the phase change of the interference, this would allow to extract the shift (or gradient) of the phase shift that is caused by refraction in the sample.

Unfortunately the phase shift of the interference pattern is typically too small to be directly spatially resolved. The resolution powers of most X-ray detectors would not allow this. Therefore in order to "sample" this interference pattern phase shift, a second attenuation rating $G_2$ with the same period p2 as the interference pattern is placed at a distance l from grating $G_1$. The actual extraction of the interference pattern phase shift (and hence that of the phase gradient caused by the sample) can be achieved in a number of different ways according to different embodiments that are all envisaged herein.

In general what is required for the differential phase extraction is a relative motion between the detector D and at least one of the gratings. This can be achieved in one embodiment by using an actuator to laterally (that is along x direction parallel to the gratings), move for instance, analyzer grating $G_2$ across different, discrete grating positions and then measure at each grating position the intensity at each pixel px. The intensity at each pixel will be found to oscillate in a sinusoidal fashion. In other words, each pixel records a time series of different intensities (at the respective pixel) as a function of time (or better as a function of the different grating positions) during motion of the analyzer grating G2. This approach ("phase-stepping") has been described by F. Pfeiffer et al in "Phase retrieval and differential phase-contrast imaging with low-brilliance X-ray sources," Nature Phys. Lett. 2, 258-261 (2006).

As described for instance on page 29104, equations (1a), (1b) in the Epple reference cited earlier, the oscillating intensity signal at each pixel px "encodes" the desired phase shift of the interference pattern along with the absorption caused by the sample and the de-coherence caused by the sample (also known as "small angle scattering"). In this sense, differential phase contrast imaging is a misnomer as the technique does not only yield the differential phase contrast but also the absorption signal (that is traditionally measured in radiography) and a third quantity, a de-coherence signal, that relates to the degree of scattering suffered by the X-ray (also referred to as small angle scattering). In other words, the pixel signals furnish three different image signal channels, each for a separate one of the three physical effects, i) absorption, ii) de-coherence and iii) refraction. In yet other words the presence of a sample will introduce a threefold disturbance on the incoming X-ray wave front and differential phase contrast imaging allows capturing each of these disturbances by way of three quantities or parameters A (absorption), V (de-coherence), $\Delta\varphi$ ($\sim\Phi\Delta$) (phase shift). The three quantities can be obtained by processing the detector signals per pixel px into numerical form by data acquisition circuitry (not shown) which includes in particular A/D conversion circuitry. The numbers are then processed by a Fourier Analyzer FA or by a curve fitting operation to obtain the parameters A, V, $\Delta\varphi$, per pixel. The collection of these (imaging) parameters can then be processed by a processing unit PR. For instance, some or all of the parameters may be mapped to a color or grey value palette and are then rendered for view on the screen MT as respectively an absorption image, a de-coherence image ("dark field image") or a phase contrast image. The degree or amount of disturbance for each of the three physical effects (absorption, de-coherence and differential phase contrast), are measured by the three respective quantities retrievable from the Fourier analysis or other curve fitting operation performed by module FA.

As briefly hinted at earlier, the sampling of the interference pattern may not necessarily be achieved by moving gratings $G_1$, $G_2$ relative to each other. In other embodiments, for instance, in a mammography imaging system, the two gratings $G_1$ and $G_2$ are mounted (one on top of the other) and rigidly onto the detector. It is then the detector together with those two gratings that is laterally moved in a scanning motion past the sample and it is this motion that can then be used (instead of the phase stepping described above) to obtain the three imaging quantities/parameters A, V, $\Delta\varphi$.

The differential phase contrast imaging system IM as described above may be, (as mentioned) in one embodiment a mammography system of the slot or slit design, or it may be a CT imaging system or it may be a rotational C-arm radiography system.

For differential phase contrast imaging to work, the above mentioned (Talbot-) distances D and l must be accurately observed. They can be computed for instance as described by E Roessl et al, "Clinical boundary conditions for grating-based differential phase-contrast mammography", Philosophical Transactions of The Royal Society (A) Mathematical, Physical and Engineering Sciences, 6 Mar. 2014, Vol 372 No 2010. Also, the above signal processing assumes a perfect alignment and perfect manufacturing of the hardware involved, in particular that of the gratings and the detector. However, as a matter of practical reality there are always inaccuracies that will undermine the accuracy of the measurements and hence of the above signal processing and hence of the computations involved. For instance, pixels might be damaged or might not be responsive in a way they should be, or the gratings may be slightly warped or tilted. In order to account for those imperfections which vary in degree from a particular imaging system used, a calibration procedure is called for. For the calibration procedure, a specifically designed calibration phantom body PB is proposed herein. The phantom body PB is placed into the examination region and is then imaged as it were an actual object of interest, such as a breast or other anatomical part or whatever object one may wish to image.

The phantom body PB which will be described in further detail below is so designed that it will cause a known degree of disturbance at known pixel positions in respect of the physical effects i)-iii) introduced above. Because the degree of each of the disturbances is known, the response at the Fourier analyzer FA can be theoretically predicted. In general however, because of the hardware imperfections, there will be a deviation from this expected theoretical value. This deviation can be expressed as ratios between the imaging quantities as computed from the actually measured detector signal and the theoretically predicted imaging quantities. The ratios can then be stored as calibration correction values A', V', $\Delta\varphi'$ per pixel.

Then, in a future imaging session, when a sample of interest is then introduced into the examination region and imaged as above described, the stored correction values A', V', $\Delta\varphi'$ can then be applied to the imaging quantities derived when processing the detector signals as per said object to so correct for the imperfections of the imaging system. In other words, the calibration correction values are used for image correction. The calibration procedure will need to be repeated now and then because hardware imperfections are in general not static but are subject to change due to thermal variations, etc.

Figure 2:
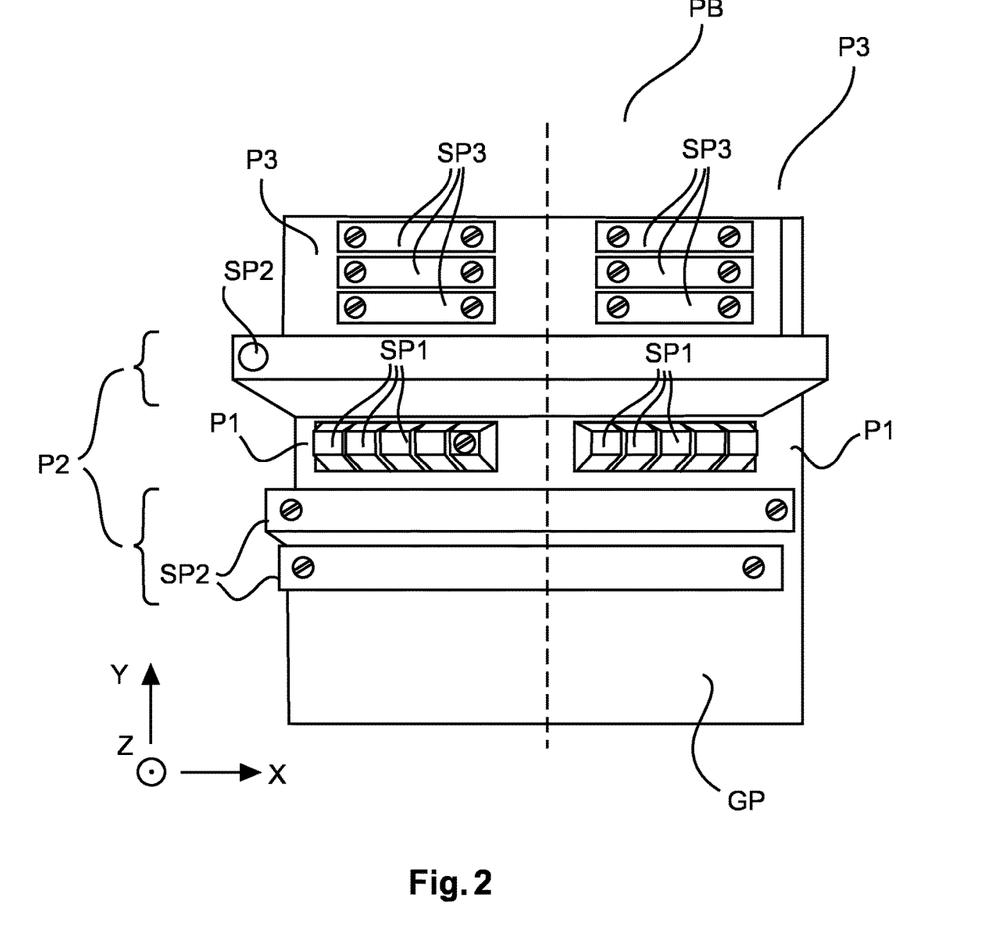
FIG. 2 shows a plan view of a calibration phantom.
Figure 3:
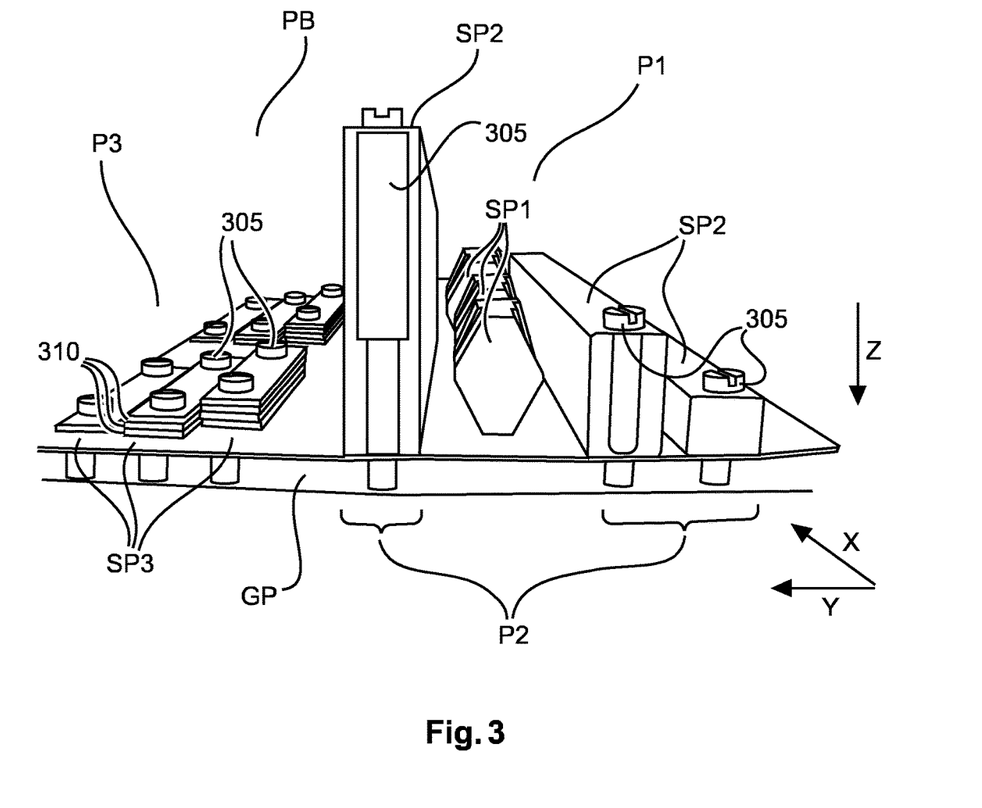
FIG. 3 shows a side elevation of the calibration phantom of FIG. 1.
Figure 4:
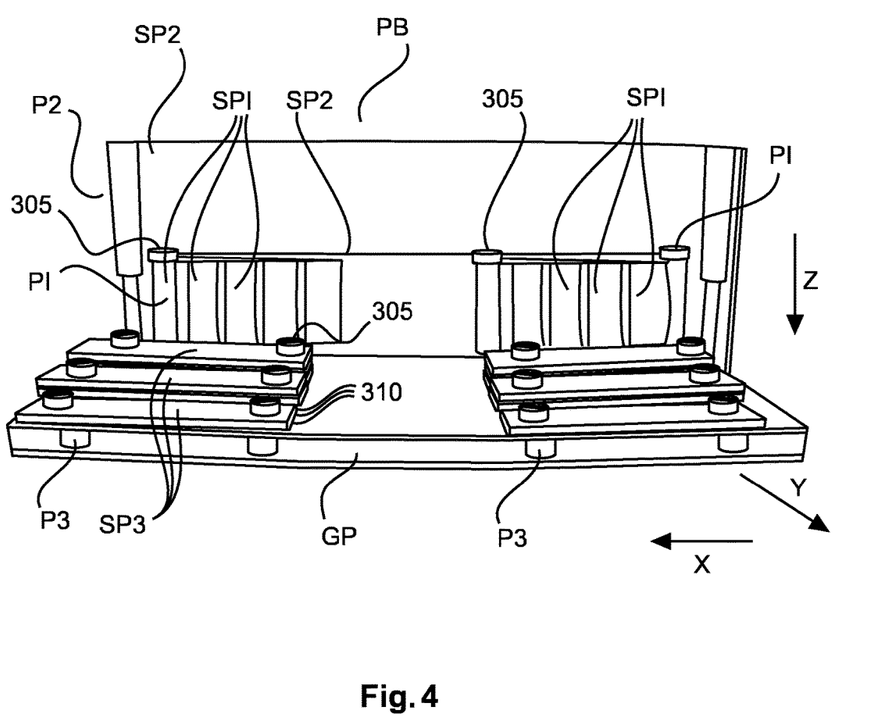
FIG. 4 shows a second side elevation of the calibration phantom of FIG. 1.

With reference to FIGS. 2-4 now there are shown different views of a phantom body according to one embodiment. In general, the phantom body is so designed that it allows calibration of each of the three imaging quantities A, V, $\Delta\varphi$ or channels simultaneously.

FIG. 2 affords a plan view along the z-axis on the phantom body PB. The z-axis is taken as the propagation direction of the X-ray beam (or wave front) XB. The z-axis in FIG. 2 extends into the paper plane. In use, that is when placed in the examination region between detector and X-ray source, the phantom body is supported by an examination table extending into the examination region (not shown in the Figs.).

As the plan view of FIG. 2 shows, the phantom body PB comprises at least (in some examples exactly three) distinct parts P1-P3. The three parts P1, P2, P3 will be referred to herein respectively as the phase contrast part P1, the absorption part P2 and the de-coherence part P3. In the embodiment of FIG. 2 each of the parts P1, P2, P3 is formed as respective blocks or groups of blocks. The blocks, P1, P2, P3 are mounted on a ground plate GP by suitable attachment means. The embodiment of phantom body PB has a mirror symmetry with respect to an axis of symmetry (shown in dashed lines) in the x-y plane forming two "leafs" of the phantom body PB, one on either side of said axis of symmetry. The following description will focus therefore on the blocks P1-P3 on one leaf of the phantom body with the understanding that the below explanation are of equal application to the blocks arranged in the other leaf Although block P2 with its three sub-parts/blocks SP2 are shown to extend across the symmetry axis, this may not be so necessarily. For instance, blocks P2 may run only half way (or less) along the axis as blocks SP3,SP1 of blocks P3,P1 do. In fact, it is the restriction to the blocks of only one of the two leafs that forms a (smaller) phantom body PB in its own right according to one embodiment.

Each of the blocks P1, P2, P3 is so configured that it causes a single one of the three disturbances (absorption, phase shift, de-coherence) at a higher degree than the other two parts. For instance, the absorption block P2 is formed from such a material that the absorption disturbance caused by this block P2 is higher than the absorption caused by the remaining two block types P1 and P3. Conversely, this block P2 will act at a lower degree in respect of the other two disturbances than the two other blocks P1, P3 respectively do. The same applies to any other of the physical effects or disturbances in respect of the other two blocks. For instance, the phase shift caused by the specialist phase shift block P1 occurs at a higher degree than the refraction caused by any of the other block types P2 and P3. The same holds true for de-coherence. In other words each of the blocks P1, P2, P3 are dedicated to a particular single one of the three disturbance types, with each block acting more prominently in respect of a different and single one of the three disturbances. In short the three blocks P1-P3 act complementarily in respect of degree or how strong they cause the respective disturbances. This complementarity allows an accurate and also a simultaneous acquisition of the calibration parameters A, V, $\Delta\varphi$.

The respective parts, P1, P2, P3, dedicated to a different and single one of the physical effects/disturbance, are spatially distributed across the x-y plane (that is, the plane perpendicular to the wave propagation direction along the z-axis) and will therefore come to lie over different parts of detector pixels px and/or gratings $G_1$, $G_2$ when the phantom body is placed in the examination region. Because different parts of the phantom body are dedicated to different ones of the three types of the physical disturbances, the respective parts of the phantom body can be spatially registered and associated with respective underlying portions of detector and the gratings. Because the dimensions of the detector and the phantom body are used different parts of the detector will be used to acquire different calibration parameters. For instance, the signals picked up by those parts of the detector pixels that come to lie exactly under (or as the case may be above) the absorption block P2 will be used exclusively for determining the absorption correction or calibration parameters. The same applies respectively to the remaining pixels that come to lie under (or over as the case may be, for instance when the phantom is used in CT) one of the other phantom body parts P1 or P3. Because this spatial phantom body-detector registration and the various detector pixel positions are assumed known, it can be determined for each pixel (for instance by logic circuitry arranged upstream of Fourier Analyzer FA) whether it is the A, V, or $\Delta\varphi$ value that is to be retained for that particular pixel, depending on which phantom part P1-P3 said pixel happens to be spatially associated with. The respective pixel coordinates are forwarded to the Fourier analyzer to so inform same to provide as output only respective ones of the image calibration parameters A, V, $\Delta\varphi$ for said pixel.

As can be seen in FIG. 2, the respectively dedicated blocks P1, P2, P3 are not monolithic but are rather integrally formed by a plurality of sub-parts SP1, SP2 and SP3 respectively. But that is not to say that monolithic embodiments are not envisaged herein. In a non-monolithic embodiment, the absorption part P2 is formed of three separate sub-blocks or -parts SP2. The same holds true for the differential phase block P1 that is formed from three sub parts SP1. For instance in one embodiment, the differential phase contrast block is formed from three or more (e.g., exactly five as shown in FIG. 2) wedge elements or prisms placed adjacent to one another along the x-axis. Similarly the de-coherence block P3 is formed from three blocks SP3.

The side elevation in FIG. 3 affords a more detailed view of how the respective blocks P1, P2, P3, are constructed from their respective sub parts SP1, SP2, SP3 according to one embodiment.

For instance, each of the absorption blocks P2 are formed from three sub blocks SP1 each having a different height.

Also as per FIG. 3's side elevation, the de-coherence block P3 is formed from three sub-parts SP3. In one embodiment some or all sub-parts SP3 is/are formed as a deck of de-coherence strips 310 stacked on top of each other. The number of strips allows individually adjusting the height of de-coherence sub-blocks SP3 and hence allows adjusting the degree or amount of de-coherence to be inflicting the incoming X-ray radiation wave XB.

Lastly, the phase contrast block P1 is made up (as briefly mentioned above) from a plurality of double wedged elements SP1 placed along the x-axis extending into the view conferred by FIG. 3. Each of the double wedged elements SP1 is symmetric with respect to a horizontal and vertical symmetry axis. However, each of the double wedged elements has different slopes to so cause a different degree of refraction. More particularly, each wedge is "double" in the sense that it comprises 2 pairs of slopes with opposite gradients ($\tan(+\alpha)$ and $\tan(-\alpha)$). Each element may be formed from a cuboid having 4 of its parallel edges beveled off to form 4 slopes. Any two slopes diagonally across are equal whereas any two neighboring slopes are of opposite gradient. The phase contrast block P1 may be of monolithic structure in that its elements SP1 are formed by section-wise beveling along the block's P1 longitudinal axis. Alternatively, each sub-part SP1 is formed from separate cuboid which are then placed side by side either contiguously so as to contact each other as shown in FIGS. 2-4 or are placed discretely with gaps between some or any two neighboring elements SP1. In one embodiment, additional wedges SP1 may be stacked on top (that is, in z-direction) of the block P1 or two entire blocks P1 may be stacked up in z-direction. In this manner a phase shift booster can be constructed because the wave front that propagates across the stack of phase contrast blocks will experience the sum of refraction when passing through the two or more (double-)wedges SP1.

An advantage of having the blocks P1, P2, P3, made up of three or more distinctive sub-parts SP1-SP3 is that accuracy of the calibration can be increased. Having in each block at least three different types of graduations for each of the three different effects i)-iii) will allow fitting three or more variables to the respective measured values as recorded by the detector pixels. More particularly, the correction parameters A, V, A are computed in one embodiment by a curve fitting operation which becomes more stable if one records three or more occurrences of the respective disturbance i)-iii) at different degrees. For instance, having the absorption block P2 comprise three sub-blocks SP2 of different heights would allow recording absorption at three different degrees, highly absorbing block which is the highest block, a block with low absorption which is the lowest block SP2 and a middle sized block having a height in between the highest and lowest to record an absorption level in between the two extremes. The graduations across the respective sub-parts notwithstanding, it is still assured that respective type of disturbance caused by the sub-parts of one block, although different, are still at a higher degree than the disturbance of the same type i), ii) or iii) caused by any sub-part of the two other blocks. By way of example, in the phase contrast block P1, although its components (the double wedges SP1 that is) cause different refractions, each of those refractions is still larger than any of the refractions caused by the other remaining blocks P2 and P3 (that is by their sub-parts SP2,SP3). An analogous situation holds true for the other blocks P2, P3 with respect to the pre-dominant disturbances caused by those blocks.

However, the number of graduations in each block as shown in FIGS. 2 and 3 are according to one embodiment only and each other number, preferably at least three, is also envisaged herein. Preferably however the number of graduations for each block is three or more, for instance, five, seven or even larger.

As can be seen in FIGS. 2 and 3 the respective blocks or sub-blocks have holes, at least two per block, extending in the direction of the wave propagation Z through the respective blocks. The holes are threaded to receive a respective bolt or screw 305 which is used to attach the respective blocks to the ground plate GP. In one embodiment the bolts 305 are formed from the same material as the respective block but this may not necessarily be so.

FIG. 4 affords a side elevation this time along the y-direction of the phantom body PB and "through" the transparent sub-block SP1 between blocks P1,P3.

Although FIGS. 2-4 show each of the parts P1-P3 formed non-monolithically, this is not limiting as some or all of the parts P1-P3 may be arranged in alternative embodiments as a single monolithic block with the sub-parts defined therein. For example, the absorption block may be arranged as a single block with a stepped surface each step defining one of the sub-parts SP1-3.

As shown in FIGS. 2-4 the respective block or block groups P1-P3 are shown as an inter-leaved embodiment. For instance, the differential phase contrast block P1 is arranged between two adjacent absorption blocks SP2. However, this interleaving is according to one embodiment only and other embodiments are envisaged where the groups are not inter-leaved but the respective sub-blocks P1, P2, P3 are strictly grouped together to form non-inter-leaved de-coherence phase contrast and absorption blocks P1, P2, P3. As can be gathered from FIGS. 2, 3, 4 there are gaps between the respective blocks P1-P3 and/or between the respective sub-parts SP-SP3. Also, the particular interleaving as shown in FIG. 2 (that is, that of blocks P1 and P2) is exemplary and other interleaving combinations are also envisaged herein. In other words, the particular sequence (in y direction) of blocks P1-P3 is an exemplary embodiments and other block/sub-block sequences are also envisaged. The particular sequential arrangement as per FIG. 2 has provided good calibration results.

However alternative embodiments are envisaged where all or some of the respective blocks P1-P3 or sub-blocks SP1-SP3 are placed in direct contact to each other on the ground plate or are formed or otherwise defined in a single block.

Figure 5:
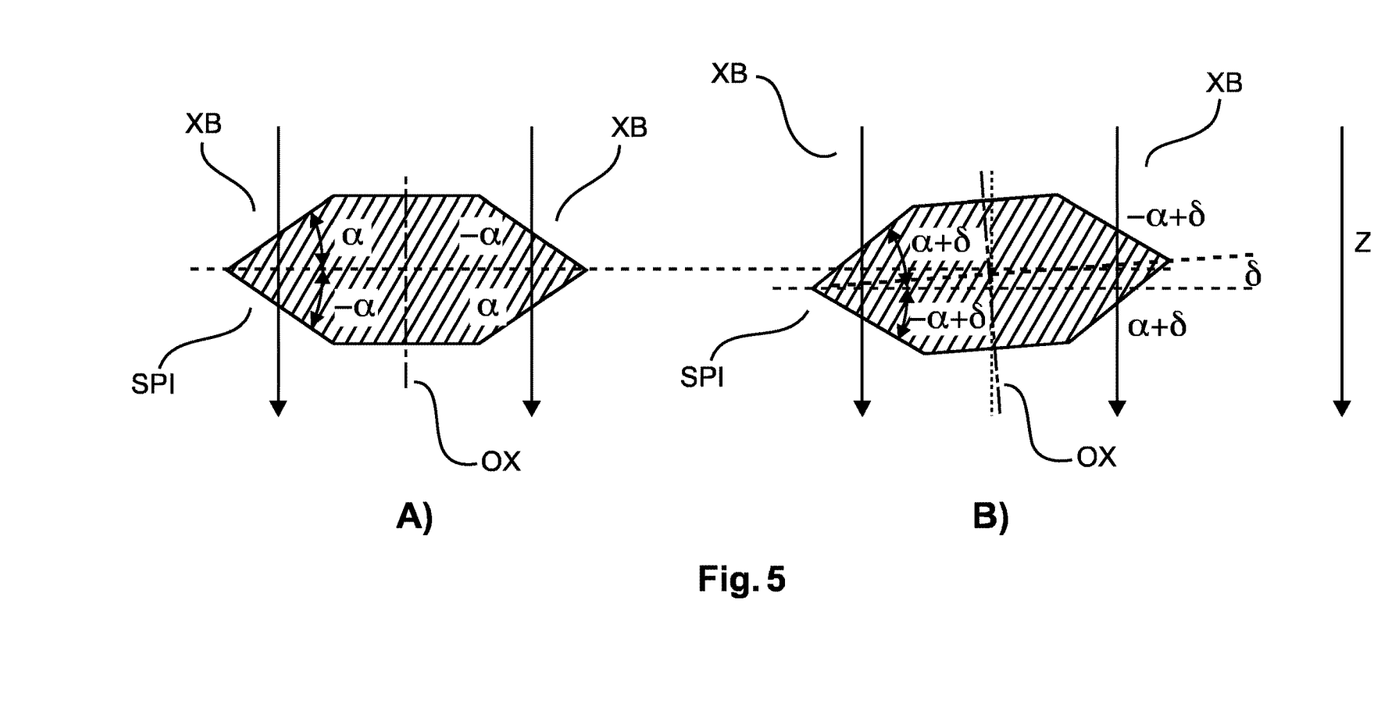
FIG. 5 shows a side elevation of a part of the phantom of FIG. 1.

With reference to FIG. 5A, B the phase contrast block P1 includes a mechanism to help in aligning the phantom PB with respect to the optical axis OX.

FIG. 5A) shows the situation of a well aligned system whereas FIG. 5B) shows an instance of a slightly misaligned system, the misalignment being describable by an angular displacement $\delta$ relative to the optical axis OX. It has been observed that special care is required when aligning the calibration phantom PB in the examination relative to X-ray source XR and/or detector D and/or gratings $G_0$-$G_2$. For the case of the phase contrast signal itself, the density gradient of a material transition with respect to a direction perpendicular to the X-ray beam is the factor that most affects the differential phase in DPCI. In FIG. 5A), the density gradient is represented by the angle $\alpha$ [or better $\tan(\alpha)$] of the wedge. For very steep gradients (large $\alpha$) a slight angular misalignment $\delta$ of the wedge will lead to significant errors. In order to put things right, the pair of wedges is used having the opposing gradients as described above. As can be seen in FIG. 5B), the sum of the magnitudes of the effective gradients is almost insensitive to a small misalignment angles $\delta$. In other words, the special symmetry of the double wedges affords a "sea-saw" effect (that is pivoting about the double wedges central point), in that an increase in gradients on one side is offset by a decrease in gradient on the other side by the same amount but in opposite orientation.

As mentioned earlier, the phantom body PB has a mirror symmetry along the symmetry axis shown in dashed lines in FIG. 2. In other words, this double leaf embodiment has a pair of phase contrast blocks P1 and a pair of de-coherence blocks P3 (each as previously described) and each arranged around the axis of symmetry with the three sub-parts SP2 of the absorption blocks P2 extending across the axis of symmetry. Other arrangements are also envisaged where it is either one (or both) of blocks P1, P3 that extending across the axis instead of or in addition to the absorption block P2.

The above symmetry considerations are not to imply that asymmetric block arrangements are not excluded herein.

They are not. Under certain space restrictions in the examination region of the imager, asymmetric arrangements are called for.

The left or right hand sides of FIG. 2 form primitive phantom body that can be mounted together on a single ground plate to so construct more complex symmetric or asymmetric phantom bodies that are formed from two (as shown in FIG. 2) or more primitive phantom bodies such as from 4, 6, 8 or any other number of primitive phantom bodies for the case of symmetric arrangements. Using such complex phantom bodies that are those composed of a plurality of primitive phantom bodies (such as the one on the left or right hand side of FIG. 2) has the advantage that the calibration operation can be "localized" to different portions of the detector plane and/or gratings. In fact, in some imaging systems such as in mammography, the interferometric gratings cannot be manufactured to any desired field of view size. More often than not the required field of view is much larger than the size of the different gratings $G_1$. $G_2$ or $G_0$. In these contexts, one solution is to use a tiling of individual gratings to so build up that are the required size of the field of view. For imaging systems with grating tilings, a complex phantom may be beneficial because each of the primitive phantoms that make up the complex phantom can be used to calibrate different ones of the gratings in the grating tiling.

Although the different phantom body parts P1, P2, P3 are shown as blocks or cuboids in the embodiments according to FIGS. 2-4, other geometrical shapes are also envisaged herein. That is, the different parts, P1, P2, P3, may not have necessarily a mere mirror symmetry along one axis but may have rotational symmetry. For instance, in one embodiment, the parts may be formed as cylinders or similar. More particularly, the phantom body is formed from a number of nested, hollow cylinders to form different layers P1, P2 P3 with each layer dedicated to a single one of the three physical disturbances as described above for the blocks in FIGS. 2-4. A layered structure, that is one where the parts P1-P3 are stacked onto each other are also envisaged for embodiments other than the rotational symmetric one just described. For instance, the blocks in FIG. 2-4 may be stacked onto each other in layers rather than in a side-by-side arrangement spread out on the planar surface of the ground plate GP. This stacked or layered arrangement lends itself favorably if a small overall footprint of the phantom is required. In the layered embodiment, the different parts are preferably configured to be highly discriminatory in that the respective disturbance should be highly dominant (by a factor which can be expressed in terms of image contrast as will be explained in more detail below at FIG. 6) over the other two disturbances for any given part P1-P3 to ensure accuracy of the calibration measurements. In this sense, the "spread out" side-by-side layout as per FIGS. 2-4 is expected to be more tractable because the discriminatory requirements on the three parts P1-P3 in respect of the three disturbances i)-iii) are lower than for the stacked embodiment.

As will be appreciated from the above, the various parts P1-P3 and/or their respective sub-parts SP1-SP3 are either permanently fixed, for instance, glued, to the ground plate or are non-destructably removable by, for instance, loosening or removing the screws or bolts 305 as shown in FIG. 3 or by using releasable attachment means, snap fit, velcro, etc.

Another embodiment is envisaged where the phantom body forms essentially a phantom body kit comprising the ground plate that includes a suitable snap fittings arranged across the surface of the ground plate at suitable spatial intervals, for instance in a regular grid layout. Each of the respective sub-parts SP1-SP3 of the various parts P1-P3 are than snap-fitted into place on the ground plate according to space and shape requirements. This affords a higher flexibility over adjusting the phantom body, for instance space requirements of the imager to be calibrated.

The ground plate GP will in general be coextensive with the combined footprints of the various blocks P1-P3 but other embodiments are also envisaged where the ground plate extends beyond the footprints of the blocks as shown in FIG. 2 to ensure good footing. The ground plate may have a rectangular shape, in particular square shape, but other shapes are also envisaged the shape being largely a function of the size and shape of the examination table or support on which the phantom is to be placed during the calibration measurement.

Preferably, the absorption blocks P2 are manufactured from a (preferably homogenous) suitable polycarbonate (such as PMMA) block and the different absorption graduations are achieved by having the blocks' sub-blocks SP2 arranged at different heights. Aluminum is be used instead in some embodiments. Suitable heights for the absorption blocks are in one embodiment 2, 10, 20 and 50 mm but of course other heights are likewise envisaged depending on the absorption requirements. These blocks with a well-defined absorption have different heights, namely 10, 20, and 50 mm and serve as areas where the attenuation signal can be calibrated or evaluated.

Preferably the de-coherence blocks are manufactured from a micro glass bubble epoxy resin like Araldite as disclosed in Applicant's EP 2,283,089. The height of the de-coherence blocks are in one embodiment 1, 2 and 4 mm respectively achieved by stacking on top of each other a suitable number of de-coherence strips 310 as explained earlier with reference to FIG. 3. Any other porous or spongy or foam structure with a suitable average size of air enclosures may be suitable material from which the de-coherence blocks may be formed. Such a structure with a large number or air enclosures will exhibit only weak absorption, but due to the small glass bubbles cause relatively strong scattering and, therefore, serve as areas where the de-coherence signal can be calibrated. If the average structure of the air enclosures is large enough (that is larger than in de-coherence block), such a porous material may also be used with benefit for the phase contrast block. In this case, no sequence of different wedges are required as shown in FIGS. 2-4, but in this case the sub-parts SP1 are defined as sections with air enclosures of different average size.

The differential phase blocks P1 are manufactured in one embodiment of a homogenous PMMA block with slopes formed therein by cutting, milling or other suitable processing technique. According to one embodiment as mentioned earlier there are five pairs of wedges with different slopes or gradients. Without loss of generality and as an example of an embodiment only, the sloping angles in one embodiment are 1.5, 3, 4.5, 6 and 7° respectively. Since these wedges exhibit relatively strong phase contrast and the blocks have relatively weak attenuation and almost no de-coherence, the wedge blocks serve as an area where the differential phase signal is calibrated. In an alternative embodiment, similar to the de-coherence blocks, the absorption blocks may also be composed by a number of strips or sub blocks stackable on top of each other to so achieve the various heights.

As mentioned earlier there is a certain security gap or margin left between the various blocks and/or sub parts thereof as shown in plan view FIG. 1. Those margins ensure a more accurate calibration result because it is easier to associate respective pixels of the detector with the above or below lying blocks. To ensure the accurate calibration result gaps of 5-10 mm in between the various blocks and sub blocks are preferred.

Figure 6:
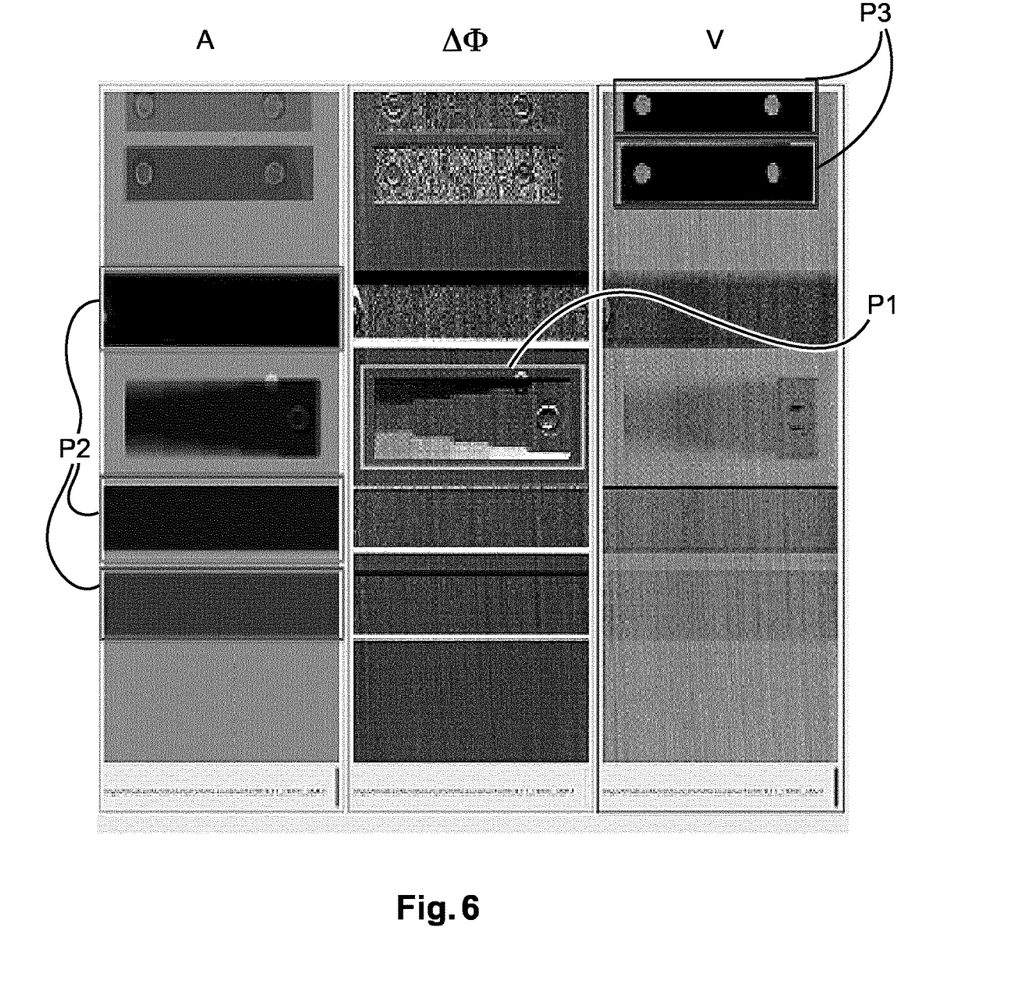
FIG. 6 shows images of the phantom of FIG. 1 as recorded by a phase contrast imaging system.

With reference to FIG. 6 there are shown reconstruction results for a typical set of calibration parameters which have been rendered as images. For simplicity in FIG. 6 the same reference signs P1-P3 have been used to indicate the various images as for indicating the blocks in FIGS. 2-4. The three rows correspond, from left to right, to the absorption images, the differential phase contrast images and the de-coherence images. The three rows of images show clearly the complimentary character of the three block types P1-P3. In each row the highest contrasts are achieved by exactly one of P1 or P2 or P3 blocks. For instance, the middle row shows the highest contrast for the phase contrast blocks P2 whereas the remaining blocks P1 or P3 show a negligible contrast only for the refraction signal. The phase contrast, which is caused by the different slopes of the wedge blocks SP2, can be observed quite well (there is also some contribution from the edges of the absorption blocks although this could be next to avoided by using a suitable X-ray beam XB shape, such as a parallel beam instead of a fan beam for instance). Also, see the right most column where the de-coherence image is shown, the de-coherence block P1 shows a good contrast whereas the other blocks do not. Similar for the absorption image in the left column: It can be observed that the three absorption blocks show relatively strong and different absorption while the Araldite block exhibits only weak absorption. For the images of FIG. 6, a "primitive" or single leaf phantom body has been used that corresponds to the right or left leaf of the double phantom embodiment of FIGS. 2-4. The different image contrast for each block or sub-block when compared across the 3 columns in FIG. 6 may be used to quantify the degree or prominence (or for the case of the sub-parts, the amount of graduation) of the different disturbances caused. For instance, the "footprint" of the absorption block (in the left column) appears at higher contrast (in one exemplary embodiment at 2 or 2-10 fold contrast) than the footprint of the other two blocks in said column. A similar observation holds true for the respective footprints of the other blocks/sub-blocks. Image contrast may be expressed in any suitable form that admits to comparison, such as the RMS (mean-root-square)-measure taken over the image pixel intensities in the respective block footprints across each of footprints in a given column of FIG. 6.

It has to be noted that embodiments of the invention are described with reference to different subject matters. In particular, some embodiments are described with reference to method type claims whereas other embodiments are described with reference to the device type claims. However, a person skilled in the art will gather from the above description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A phantom body for use in calibrating a phase contrast imaging system, comprising:
    at least three mutually distinct parts configured for causing a plurality of disturbances with respect to an X-ray beam when said X-ray beam passes through the phantom body, said plurality of disturbances including a phase shift, an absorption, and a de-coherence, wherein each disturbance of the plurality of disturbances is being caused by exactly one part of the at least three mutually distinct parts to a degree larger than other degrees with which said other disturbances are being caused by the respective two other parts of the at least three mutually distinct parts, and wherein at least one part of the at least three mutually distinct parts comprises at least three distinct sub-parts configured to graduate the respective degree of disturbance caused by said at least one part into three different sub-degrees.

2. The phantom body according to claim 1, wherein at least one part of the at least three mutually distinct parts is formed from one or more cuboids.

3. The phantom body according to claim 1, wherein at least one part of the at least three mutually distinct parts is formed from one or more rotation symmetric solids.

4. The phantom body of any one according to claim 1, wherein the three or more sub-parts of at least one part of the at least three mutually distinct parts are grouped together.

5. The phantom body according to claim 1, wherein the three or more sub-parts of at least one part of the at least three mutually distinct parts are interleaved with one or more sub-parts from at least another one of the two other parts of the at least three mutually distinct parts.

6. The phantom body according to claim 1, wherein said phantom body is symmetric.

7. The phantom body according to claim 1, wherein the part of the at least three mutually distinct parts that causes the highest intensity of phase contrast disturbance, is formed from a plurality of wedges each wedge having a different wedge slope gradients configured to cause a different phase gradient and each wedge forming one of the sub-parts of said part.

8. The phantom body according to claim 7, wherein at least one of the wedges is formed as a double wedge with opposed slope gradients.

9. The phantom body according to claim 1, wherein at least one of the parts of the at least three mutually distinct parts is formed from any one of Polycarbonate, Poly-methyl-methacrylate, Aluminum, and epoxy resin.

10. The phantom body according to claim 1, wherein the part of the at least three mutually distinct parts that causes the highest degree of de-coherence disturbance, is formed from a structure having a plurality of air enclosures.

11. The phantom body according to claim 1, wherein said parts are defined on a common ground plate.

12. A phantom body system including a plurality of phantom bodies as per claim 1, wherein said phantom bodies are being mounted on a common ground plate.

13. A phantom body system according to claim 12, wherein the plurality of phantom bodies are arranged on said ground plate in a symmetric manner.

14. A method of calibrating a phase contrast imaging system, the method comprising:
   emitting an X-ray beam;
   providing a phantom body comprising at least three mutually distinct parts; and
   causing a plurality of disturbances with respect to the X-ray beam when said X-ray beam passes through the phantom body, said plurality of disturbances including a phase shift, an absorption, and a de-coherence, wherein each disturbance of the plurality of disturbances is being caused by exactly one part of the at least three mutually distinct parts to a degree larger than other degrees with which said other disturbances are being caused by the respective two other parts of the at least three mutually distinct parts, and wherein at least one part of the at least three mutually distinct parts comprises at least three distinct sub-parts configured to graduate the respective degree of disturbance caused by said at least one part into three different sub-degrees.

15. The method according to claim 14, wherein at least one part of the at least three mutually distinct parts is formed from one or more cuboids.

16. The method according to claim 14, wherein at least one part of the at least three mutually distinct parts is formed from one or more rotation symmetric solids.

* * * * *